United States Patent

Zink

[11] Patent Number: 5,395,948
[45] Date of Patent: Mar. 7, 1995

[54] FLUORAN COLOR FORMERS

[75] Inventor: Rudolf Zink, Therwil, Switzerland

[73] Assignee: Ciba-Geigy Corporation, Ardsley, N.Y.

[21] Appl. No.: 29,216

[22] Filed: Mar. 10, 1993

[30] Foreign Application Priority Data

Mar. 17, 1992 [CH] Switzerland ............... 862/92
Nov. 10, 1992 [CH] Switzerland ............ 3475/92

[51] Int. Cl.⁶ ............... C07D 311/88; C07D 413/12; C07D 403/00; B41M 5/20
[52] U.S. Cl. ................... 549/225; 503/221; 544/150; 544/359; 546/187; 548/517
[58] Field of Search ............. 549/225, 226, 445; 503/222, 221; 544/150, 359; 546/187; 548/517

[56] References Cited

U.S. PATENT DOCUMENTS

| 3,624,107 | 11/1971 | Lin | 549/225 |
|---|---|---|---|
| 3,627,787 | 12/1971 | Lin | 549/226 |
| 3,637,757 | 1/1972 | Lin | 549/225 |
| 3,641,011 | 2/1972 | Lin | 549/225 |
| 3,713,863 | 1/1973 | Lin | 503/221 |
| 3,715,226 | 2/1973 | Lin | 503/221 |
| 3,730,755 | 5/1973 | Lin | 503/221 |
| 3,764,369 | 10/1973 | Hoover et al. | 503/221 |
| 3,769,057 | 10/1973 | Lin | 503/221 |
| 3,769,302 | 10/1973 | Hoover et al. | 549/226 |
| 3,910,956 | 10/1975 | Hoover | 549/445 |
| 4,028,357 | 6/1977 | Crounse | 544/198 |
| 4,728,633 | 3/1988 | Satomura et al. | |

FOREIGN PATENT DOCUMENTS

| 181283 | 5/1986 | European Pat. Off. . |
|---|---|---|
| 451766 | 10/1991 | European Pat. Off. . |
| 2224456 | 10/1974 | France . |
| 1251348 | 10/1967 | Germany . |
| 2001864 | 7/1970 | Germany . |
| 2242250 | 3/1973 | Germany . |
| 2634400 | 2/1977 | Germany . |
| 989264 | 4/1965 | United Kingdom . |
| 1156725 | 7/1969 | United Kingdom . |
| 1301052 | 12/1972 | United Kingdom . |
| 1355124 | 5/1974 | United Kingdom . |
| 1418872 | 12/1975 | United Kingdom . |

Primary Examiner—Richard L. Raymond
Assistant Examiner—Deborah Lambkin
Attorney, Agent, or Firm—George R. Dohmann

[57] ABSTRACT

The invention relates to fluoran colour formers having improved fastness to sublimation and migration stability, to their preparation, to pressure-sensitive and heat-sensitive recording materials containing said compounds and to their preparation. The fluorans have the formula (I) as defined in claim 1.

25 Claims, No Drawings

FLUORAN COLOR FORMERS

Numerous fluoran colour formers for use in pressure-sensitive or heat-sensitive recording materials are already known in the art. Exacting demands are made of the storage stability of these materials and of the fastness properties of the images produced with the fluorans. There is therefore a constant search in this art to improve the sublimation fastness and the stability to migration of colour formers.

The present invention relates to fluorans, to their preparation and to the use thereof as colour formers in pressure-sensitive or heat-sensitive recording materials having enhanced sublimation fastness and the stability to migration.

The pressure-sensitive or heat-sensitive recording material comprises at least one colour former of formula (I)

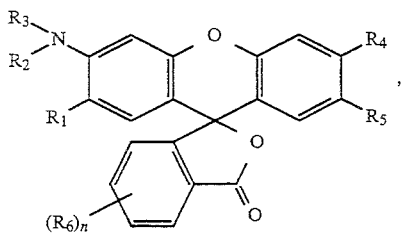

wherein
$R_1$ is hydrogen or $C_1$–$C_4$alkyl;
$R_2$ and $R_3$ are each independently of the other hydrogen; $C_1$–$C_8$alkyl; unsubstituted or $C_1$–$C_4$alkyl- or halogen-substituted $C_4$–$C_7$cycloalkyl; unsubstituted phenyl or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$–$C_4$alkyl; 2-tetrahydrofuranyl, or
$R_2$ and $R_3$ together with the linking nitrogen atom are an unsubstituted or $C_1$–$C_4$alkyl-substituted pyrrolidino, piperidino, morpholino, thiomorpholino or piperazino ring;
$R_4$ is hydrogen, hydroxy or $C_1$–$C_4$alkyl;
$R_5$ is nitro; $SO_2R_7$; $SO_2OR_8$; $SO_2NR_9R_{10}$; $COR_{11}$; $CONR_9R_{10}$; or $C_1$–$C_4$haloalkyl; an unsubstituted or a halogen- or hydroxy-substituted 2-triazinyl or 1-benzotriazolyl radical;
$R_6$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_{11}$;
n is 0; 1; 2; 3; or 4;
$R_7$ is $C_1$–$C_8$alkyl; or $C_1$–$C_8$haloalkyl; unsubstituted phenyl or phenyl-$C_1$–$C_4$alkyl or phenyl or phenyl-$C_1$–$C_4$alkyl which is substituted by halogen, $C_1$–$C_4$alkyl, $C_1$–$C_4$haloalkyl or $C_1$–$C_4$alkoxy;
$R_8$ is hydrogen, $C_1$–$C_8$alkyl; $C_1$–$C_8$haloalkyl; unsubstituted phenyl or phenyl-$C_1$–$C_4$alkyl or phenyl or phenyl-$C_1$–$C_4$alkyl which is substituted by halogen, $C_1$–$C_4$alkyl, $C_1$–$C_4$haloalkyl, $C_1$–$C_4$alkoxy;
$R_9$ and $R_{10}$ are each independently of the other hydrogen; or $C_1$–$C_8$alkyl;
$R_9$ and $R_{10}$ together with the linking nitrogen atom are an unsubstituted or a $C_1$–$C_4$alkyl-substituted pyrrolidino, piperidino, morpholino, thiomorpholino or piperazino ring; and
$R_{11}$ is hydrogen, hydroxy; $C_1$–$C_8$alkyl; $C_1$–$C_8$alkoxy; $C_1$–$C_8$haloalkyl; unsubstituted phenyl or phenyl which is substituted by halogen, $C_1$–$C_4$alkyl, $C_1$–$C_4$haloalkyl, or $C_1$–$C_4$alkoxy; or phenyl-$C_1$–$C_4$alkyl or phenyl-$C_1$–$C_4$alkoxy,
with the proviso that 3-diethylamino-7-methylsulfonylfluoran, 3-diethylamino-7-nitrofluoran, 3-diethylamino-6-methyl-7-nitrofluoran, 3-diethylamino-7-formylfluoran, 3-diethylamino-7-carboxyfluoran, 3-diethylaminofluoran-7-carboxymethoxymethyl ester, 3-diethylamino-fluoran-7-sulfonic acid, 3-diethylamino-7-(4-ethoxyphenyl)sulfonylfluoran and 3-diethylamino-7-benzyloxyfluoran are not comprised.

In the literature the individual substituent positions at the fluoran ring are numbered differently. In this specification, the following numbering has been adopted:

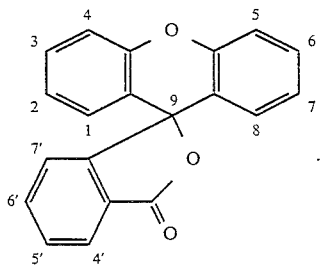

Within the scope of the above definition, the respective substituents or radicals have the following preferred meanings:

Halogen is fluoro, chloro or bromo, preferably fluoro or chloro.

Alkyl within the scope of each definition is straight-chain or branched alkyl. Examplary alkyl groups are methyl, ethyl, n-propyl, isopropyl, n-butyl, 1-methylbutyl, sec-butyl, tert-butyl, n-pentyl, amyl, isoamyl, n-hexyl, 2-ethylhexyl, n-heptyl, n-octyl, isooctyl, 1,1,3,3-tetramethylbutyl.

Haloalkyl will preferably represent $C_1$–$C_2$haloalkyl radicals such as trichloromethyl, trifluoromethyl, dichlorofluoromethyl, difluorochloromethyl, perchloroethyl, 1,1,2,2-tetrachloroethyl, 1,1,2,2-tetrafluoroethyl, 2,2,2,trichloroethyl. $R_5$ as $C_1$–$C_8$haloalkyl is preferably haloalkyl as defined above and also comprises alkyl radicals in which all or at least most of the C-H bonds are replaced by C-Cl or C-F.

Alkoxy is preferably methoxy, ethoxy, n-propoxy, isopropoxy, n-butoxy, isobutoxy, sec-butoxy and tert-butoxy. $C_1$–$C_4$Alkoxy-$C_1$–$C_4$alkyl is preferably methoxymethyl, methoxyethyl, ethoxymethyl or ethoxyethyl.

Mono-$C_1$–$C_5$alkylamino is preferably methylamino, ethylamino, propylamino, butylamino and pentylamino, Di-$C_1$–$C_5$alkylamino comprises both the mixed as well as the corresponding substituted radicals such as methylethylamino, dimethylamino, diethylamino, methylpropylamino, methylbutylamino, di-n-propylamino, diisopropylamino, di-n-butylamino and di-n-pentylamino etc..

In phenyl-$C_1$–$C_4$alkyl and phenyl-$C_1$–$C_4$alkoxy the phenyl moiety can be bound through a straight-chain or branched alkyl or alkoxy chain. Phenethyl, benzyl and phenylmethoxy are preferred.

The phenyl moiety of phenyl-$C_1$–$C_4$alkyl, phenyl-$C_1$–$C_4$alkoxy and phenyl itself is preferably unsubstituted or carries up to three identical or different substituents from among those cited.

$C_3$–$C_5$Alkenyl is typically allyl, 1-propenyl or 2-pentenyl, isopropenyl or 2-butenyl. Allyl is preferred. $C_4$–$C_7$Cyclohexyl is cyclobutyl, cycloheptyl, cyclohexyl or cycloheptyl. Cyclohexyl is preferred.

The compounds of formula (I) are normally colourless or at most faintly coloured. When these sublimation-fast colour formers are brought into contact preferably with an acid developer, i.e. an electron acceptor, then, depending on the meaning of the substituents $R_1$ to $R_6$ and the developer, they produce deep orange to red images. The compounds of formula (I) are also very useful in admixture with one or more other known colour formers, typically 3,3-(bisaminophenyl)phthalides such as CVL, 3-indolyl-3-aminophenylaza- or -diazaphthalides, (3,3-bisindolyl)phthalides, 3-aminofluorans, 3,7-diaminofluorans, 3,7-diamino-6-methylfluorans, 3,6-bisalkoxyfluorans, 3,6-bisdiarylaminofluorans, leukoauramines, spiropyranes, spirodipyranes, chromenopyrazoles, chromenoindoles, phenoxazines, phenothiazines, quinazolines, rhodamine lactams, carbazolyl methanes or other triarylmethaneleuko colorants to give blue, navy blue, grey or black images.

Preferred additional colour formers are those that,-produce a black image, preferably 3,7-diaminofluorans.

The compounds of formula (I) are used to obtain blue, navy blue, grey or black images together with „the other colour formers in a ratio suitable for the desired tinctorial strength. The ratios are also influenced by the developer used in the colour reaction. They can be determined by simple experimentation. It is preferred to use from 10 to 70% of the fluoran of formula (I) (the percentages are based on the amounts of colour former) in the colour former mixtures. Amounts of about 30 to 60% are especially preferred. Such mixtures are suitable for reactive copying papers as well as for thermal papers. In the remainder of this specification, the term "colour former" comprises the colour formers of formula (I) as well as the mixtures thereof.

The compounds of formula (I) exhibit an excellent colour intensity and lightness on activated clays as well as on phenolic substrates. They are particularly suitable for use as rapidly developing colour formers in a heat-sensitive or, preferably, a pressure-sensitive recording material which may also be a copying material. They are pH-stable and have excellent solubility in the capsule oils. After exposure on a CB sheet they exhibit an insignificant decrease in colour strength (CB decline).

A pressure-sensitive material typically comprises at last one pair of sheets that contain at least one colour former of formula (I) dissolved in an organic solvent, and an electron acceptor as developer.

Typical examples of such developers are active clays such as attapulgite clay, acid clay, bentonitc, montmorillonite, activated clay such as acid-activated bentonitc or montmorillonite, and also zeolith, haloysite, silica, alumina, aluminium sulfate, aluminium phosphate, zinc chloride, zinc nitrate, zirconium dioxide, activated kaolin or any clay. As developers it is also possible to use acidic organic compounds such as ring-substituted phenols, resorcinols, salicylic acids, including 3,5-bis($\alpha,\alpha$-dimethylbenzyl)salicylic acid or 3,5-bis($\alpha$-methylbenzyl)salicylic acid or salicylates and their metal salts, e.g. zinc salts, as well as an acidic polymeric material such as a phenolic polymer, an alkyl phenol acetylene resin, a maleic acid rosin resin .or a partially or completely hydrolysed polymer of maleic anhydride with styrene, ethylene or vinyl methyl ether, or carboxymethylene. Mixtures of the cited monomers and polymers can also be used. Particularly preferred developers are acid-activated bentonite, zinc salicylates or the condensates of p-substituted phenols with formaldehyde. These,last mentioned compounds may also be modified with zinc. Zinc salicylates are disclosed, inter alia, in EP-A-181,283 or DE-A-2,242,250.

The developers may also be used in admixture with other basically inert or substantially inert pigments or with other auxiliaries such as silica gel or UV absorbers, e.g. 2-(2'-hydroxyphenyl)benzotriazoles. Examples of such pigments ,are: talcum, titanium dioxide, alumina, aluminium hydroxide, zinc oxide, chalk, clays such as kaolin, as well as organic pigments, e.g. urea/formaldehyde condensates (BET surface area: 2–75 $m^2$/g) or melamine/formaldehyde condensates.

The colour former produces a coloured image at those points where it comes into contact with the electron acceptor. To prevent the colour formers contained in the pressure-sensitive recording material from becoming active prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured image is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a halogenated paraffin, benzene or diphenyl, for example chloroparaffin, trichlorobenzene, monochlorodiphenyl or trichlorodiphenyl, and also esters such as uicresyl phosphate, di-n-butyl phthalate, dioctyl phthalate, trichloroethylphosphate, an aromatic ether such as benzylphenyl ether, a hydrocarbon oils such as paraffin or kerosene, aromatic hydrocarbons, an alkylated derivative (e.g. containing isopropyl, isobutyl, sec- or tert-butyl groups) of diphenyl, naphthalene or terphenyl; dibenzyl toluene, partially hydrogensted terphenyl, mono- to tetra-$C_1$–$C_3$alkylated diphenylalkanes, dodecylbenzene, benzylated xylenes, phenyl xylyl ethane or other chlorinated or hydrogensted condensed aromatic hydrocarbons. Mixtures of different solvents, especially mixtures of paraffin oils or kerosene and diisopropylnaphthalene or partially hydrogensted terphenyl, are often used to obtain optimum solubility of the colour formers, a rapid and intense coloration, and a viscosity which is advantageous for the microencapsulation. For the encapsulation, the novel phthalides are distinguished by the feature that they are readily soluble and are pH-resistant in a pH range from 4 to 10.

The capsule walls can be formed evenly around the droplets of the colour former solution by coacervation. The encapsulating material is described e.g. in U.S. Pat. No. 2,800,457. The capsules may also be conveniently formed from an aminoplast or a modified aminoplast by polycondensation, as described in British patent specifications 989,264, 1,156,725, 1,301,052 and 1,355,124. Also suitable are microcapsules which are formed by interfacial polymerisation, e.g. capsules formed from polyester, polycarbonate, polysulfonamide, polysulfonate, but preferably from polyamide or polyurethane.

The microcapsules containing the colour formers of formula (I) can be used for the production of a wide variety of known kinds of pressure-sensitive copying material. The various systems differ substantially from one another in the arrangement of the capsules, of the colour reactants, and of the support.

The colour formers of formula I can be used with advantage as mixture components in microencapsulated colour former systems. The sublimation fastness of the fluorans of formula I is in this connection particularly advantageous. As mentioned at the outset, the fluorans of the prior art which produce yellow and orange images exhibit more of a sublimation or migration tendency than the other colour formers used in such mixtures. The mixture ratio must therefore take into account the properties of the component that has the most pronounced sublimation tendency. In contradistinction thereto, the sublimation fastness of the compounds of this invention matches that of the other mixture components. The advantages accruing therefrom are obvious: when choosing the mixture components it is no longer necessary to take special account of more readily sublimable components of the colour former system. The enhancement of migration stability in the novel colour former mixtures has a particularly advantageous effect on the developed image. Even after prolonged storage of the copying material, the image retains its sharp outlines and does not become blurred.

A preferred arrangement is that in which the encapsulated colour former is in the form of a layer on the back of a transfer sheet and the electron acceptor (colour developer) is in the form of a layer on the face of a receiver sheet. Another arrangement of the components is that wherein the microcapsules which contain the colour former, and the developer, are in or on the same sheet in the form of one or more individual layers, or the developer is incorporated in the support.

The capsules are preferably secured to the support by means of a suitable binder. As paper is the preferred support, these binders are principally paper-coating agents such as gum arabic, polyvinyl alcohol, hydroxymethyl cellulose, casein, methyl cellulose, dextrin, starch or starch derivatives or polymer latices. These latter are typically butadiene/styrene copolymers or acrylic homopolymers or copolymers.

The paper employed comprises not only normal paper made from cellulose fibres, but also paper in which the cellulose fibres are replaced (partially or completely) by synthetic polymer fibres. The support may also be a plastic sheet.

The copying paper may also comprise a capsule-free layer that contains the colour former and a colour developing layer wherein the colour developer containing at least one inorganic metal salt of a polyvalent metal, preferably a halide or nitrate such as zinc chloride, tin chloride, zinc nitrate or a mixture thereof.

The compounds of formula (I) may also be used as colour formers in a thermoreactive recording material. This recording material usually comprises at least one support, one or more than one colour former, one electron acceptor, and optionally also a binder and/or wax. If desired, the recording material may also comprise an activator or sensitiser.

The colour formers of formula I may be used with advantage as mixture components in thermoreactive colour former systems. The storage stability (hot and/or moist) and the low background discolouration of the inventive fluorans are particularly advantageous.

Thermoreactive recording systems comprise, for example, heat-sensitive recording or copying materials and papers. These systems are used e.g. for recording information, for example in electronic computers, teleprinters or telewriters, or in recording and measuring instruments, e.g. electrocardiographs. The image formation (marking) can also be effected manually with a heated pen. Laser beams can also be used to produce heat-induced images.

The thermoreactive recording material can be composed such that the colour former is dispersed or dissolved in one binder layer and the developer is dissolved or dispersed in the binder in a second layer. Another possibility comprises dispersing both the colour former and the developer in one layer. By means of heat the layer or layers are softened at specific areas and the desired colour develops at once at those areas where heat is applied.

Suitable developers are the same electron acceptors as are used in pressure-sensitive papers. Examples of developers are the clays and phenolic resins already mentioned, or also the phenolic compounds disclosed e.g. in German Offenlegungsschrift 1 251 348, for example 4-tert-butylphenol, 4-phenylphenol, methylene bis(p-phenylphenol), 4-hydroxydiphenyl ether, $\alpha$-naphthol, $\beta$-naphthol, 4-hydroxydiphenylsulfone, 4-hydroxy-4'-methyldiphenylsulfone, methyl or benzyl 4-hydroxybenzoate, 4'-hydroxy-4-isopropoxydiphenylsulfone, 4,4'-cyclohexylidenediphenol, 4,4'-isopropylidenediphenol, 4,4'-isopropylidenebis(2-methylphenol), an antipyrine complex of zinc thiocyanate, a pyridine complex of zinc thiocyanate, 4,4'-bis(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid; citric acid, citraconic acid or succinic acid.

It is preferred to use fusible, film-forming binders for making the thermoreactive recording material. These binders are normally water-soluble, whereas the lactams and the developer are sparingly soluble or insoluble in water. The binder should be able to disperse and fix the colour former and the developer at room temperature.

When heated, the binder softens or melts, so that the colour former comes in contact with the developer and a colour is able to form. Examples of binders which are soluble, or at least swellable, in water are hydrophilic polymers such as polyvinyl alcohol, polyacrylic acid, hydroxyethyl cellulose, methyl cellulose, carboxymethyl cellulose, polyacrylamide, polyvinyl pyrrolidone, gelatin, starch or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former mad the developer are contained in one layer in a water-soluble binder.

To ensure the stability of the heat-sensitive recording material or the density of the developed image, the material may be provided with an additional protective layer. Such a protective layer will normally consist of water-soluble and/or water-insoluble resins which are conventional polymeric materials or aqueous emulsions of these polymeric materials.

The thermoreactive layers and resin coatings may contain further auxiliaries. To improve the degree of whiteness, to facilitate the printing of papers, and to prevent the heated pen from sticking, these layers may contain e.g. talcum, titanium dioxide, zinc oxide, alumina, aluminium hydroxide, calcium carbonate (e.g. chalk), clays or also organic pigments, for example urea/formaldehyde polymers. To effect the colour formation only within a limited temperature range it is possible to add substances such as urea, thiourea, diphenyl thiourea, acetamide, acetanilide, benzene sulfanilide, bis(stearoyl)ethylenediamide, stearamide, phthalic anhydride, metal stearates such as zinc stearate, phthalonitrile, dimethyl terephthalate, dibenzyl terephthalate or other appropriate fusible products which induce the simultaneous melting of the colour former and the developer. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

A further utility of the compounds of formula (I) is the formation of a coloured image by means of the photocurable microcapsules described e.g. in German Offenlegungsschrift 3,247,488.

Preferred colour former systems are those comprising as mixture component at least one fluoran of formula I, wherein $R_1$ is hydrogen or $C_1$–$C_4$alkyl;

$R_2$ and $R_3$ are each independently of the other hydrogen; $C_1$–$C_5$alkyl; or $R_2$ and $R_3$ together with the linking nitrogen atom are an unsubstituted or $C_1$–$C_4$alkyl-substituted pyrrolidino or piperidino ring;

$R_4$ is hydrogen or $C_1$–$C_4$alkyl;

$R_5$ is nitro; $SO_2R_7$; $SO_2OR_8$; $SO_2NR_9R_{10}$; $COR_{11}$; $CONR_9R_{10}$; or $C_1$–$C_4$haloalkyl;

n is 0; 1; 2; 3; or 4;

$R_6$ is halogen when n is 1, 2, 3 or 4; or is $C_1$–$C_4$alkyl C 1-C4haloalkyl when n is 1 or 2; or, when n is 1, is nitro, $COR_{11}$, amino, mono-$C_1$–$C_4$alkylamino or di-$C_1$–$C_4$alkylamino;

$R_7$ is $C_1$–$C_4$alkyl; or $C_1$–$C_4$haloalkyl; unsubstituted phenyl or phenyl-$C_1$–$C_4$alkyl phenyl or phenyl-$C_1$–$C_4$alkyl which is substituted by halogen, $C_1$–$C_4$alkyl, $C_1$–$C_4$haloalkyl or $C_1$–$C_4$alkoxy;

$R_8$ is hydrogen, $C_1$–$C_4$alkyl; $C_1$–$C_4$haloalkyl; unsubstituted phenyl or phenyl-$C_1$–$C_4$alkyl; or phenyl or phenyl-$C_1$–$C_4$alkyl which is substituted by halogen, $C_1$–$C_4$alkyl, $C_1$–$C_4$haloalkyl or $C_1$–$C_4$alkoxy;

$R_9$ and $R_{10}$ are each independently of the other hydrogen; or $C1$-$C4$alkyl;

$R_9$ and $R_{10}$ together with the linking nitrogen atom are an unsubstituted or a $C_1$–$C_4$alkyl-substituted pyrrolidino or piperidino ring; and $R_{11}$ is hydrogen; $C_1$–$C_4$alkyl; $C_1$–$C_4$haloalkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy.

Particularly preferred colour former systems are those comprising as mixture components at least one fluoran of formula I
wherein $R_1$ is hydrogen or methyl;

$R_2$ and $R_3$ are each independently of the other hydrogen; $C_1$–$C_5$alkyl; or $R_2$ and $R_3$ together with the linking nitrogen atom are an unsubstituted pyrrolidino or piperidino ring;

$R_4$ is hydrogen or methyl;

$R_5$ is nitro; $SO_2R_7$; $SO_2NR_9R_{10}$; $COR_{11}$; $CONR_9R_{10}$; or $C_1$–$C_4$-haloalkyl;

n is 0, 1, 2, 3 or 4;

$R_6$ is halogen when n is 1, 2, 3 or 4; or is methyl when n is 1 or 2; or, when n is 1, is nitro, amino, mono-$C_1$–$C_4$alkylamino or di-$C_1$–$C_4$alkylamino;

$R_7$ is $C_1$–$C_4$alkyl; or $C_1$–$C_4$haloalkyl; unsubstituted phenyl or phenyl which is substituted by halogen, $C_1$–$C_4$alkyl or $C_1$–$C_4$alkoxy;

$R_9$ and $R_{10}$ are each independently of the other hydrogen or $C_1$–$C_4$alkyl;

$R_{11}$ is hydrogen; $C_1$–$C_4$alkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy.

In particular, the invention relates to colour former systems of formula I, of preferred formula I and of particularly preferred formula I, wherein $R_5$ is $SO_2R_7$, $SO_2OR_8$, $SO_2NR_9R_{10}$, $COR_{11}$, $CONR_9R_{10}$, $C_1$–$C_4$-haloalkyl or nitro.

Among the above compounds of formula I, those compounds are preferred in which $R_5$ is $COR_{11}$ and, most especially, those in which $R_{11}$ is $C_1$–$C_4$alkyl, $C_1$–$C_4$alkoxy or phenyl-$C_1$–$C_4$alkoxy. Of preeminent interest are compounds in which $R_{11}$ is $C_1$–$C_4$alkoxy or phenyl-$C_1$–$C_4$alkoxy.

Some of the compounds of formula I are novel. A few of the compounds of formula I are described in the literature: 3-diethylamino-7-methylsulfonylfluoran in DE-A-2,155,986, 3-diethylamino-7-nitrofluoran, 3-diethylamino-6-methyl-7-nitrofluoran, 3-diethylamino7-carboxymethyl ester in U.S. Pat. No. 3,637,757, 3-diethylamino-7-formylfluoran in DE-A-2,001,864 and 3-diethylamino-fluoran-7-sulfonic acid in GB-B-1,418,871. None of these references mentions mixtures of colour formers.

The novel fluorans of this invention have the general formula (I)

(I)

wherein $R_1$ is hydrogen or $C_1$–$C_4$alkyl;

$R_2$ and $R_3$ are each independently of the other hydrogen; $C_1$–$C_8$alkyl; unsubstituted or. $C_1$–$C_4$alkyl-halogen-substituted $C_4$–$C_7$cycloalkyl; unsubstituted phenyl; or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$—$C_4$alkyl; 2-tetrahydrofuranyl, or $R_2$ and $R_3$ together with the linking nitrogen atom are an unsubstituted or $C_1$–$C_4$alkyl-substituted pyrrolidino, piperidino, morpholino, thiomorpholino or piperazino ring;

$R_4$ is hydrogen, hydroxy or $C_1$–$C_4$alkyl;

$R_5$ is nitro; $SO_2R_7$; $SO_2OR_8$; $SO_2NR_9R_{10}$; $COR_{11}$; $CONR_9R_{10}$; or $C_1$–$C_4$haloalkyl; an unsubstituted or a halogen- or hydroxy-substituted 2-triazinyl or 1-benzotriazolyl radical;

$R_6$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_{11}$;

n is 0; 1; 2; 3; or 4;

$R_7$ is $C_1$–$C_8$alkyl; or $C_1$–$C_8$haloalkyl; unsubstituted phenyl or phenyl-$C_1$–$C_4$alkyl; or phenyl or phenyl-$C_1$–$C_4$alkyl which is substituted by halogen, $C_1$–$C_4$alkyl, $C_1$–$C_4$haloalkyl, $C_1$–$C_4$alkoxy;

$R_8$ is hydrogen, $C_1$–$C_8$alkyl; $C_1$–$C_8$haloalkyl;. unsubstituted phenyl or phenyl-$C_1$–$C_4$alkyl phenyl or phenyl-$C_1$–$C_4$alkyl which is substituted by halogen, $C_1$–$C_4$alkyl, $C_1$–$C_4$haloalkyl or $C_1$–$C_4$alkoxy;

$R_9$ and $R_{10}$ are each independently of the other hydrogen; or $C_1$–$C_8$alkyl; or $R_9$ and $R_{10}$ together with the linking nitrogen atom are an unsubstituted or a $C_1$–$C_4$alkyl-substituted pyrrolidino, piperidino, morpholino, thiomorpholino or piperazino ring; and $R_{11}$ is hydrogen, hydroxy; $C_1$–$C_8$alkyl; $C_1$–$C_8$alkoxy; $C_1$–$C_8$haloalkyl; unsubstituted phenyl or phenyl which is substituted by halogen, $C_1$–$C_4$alkyl, $C_1$–$C_4$haloalkyl, or $C_1$–$C_4$alkoxy; phenyl-$C_1$–$C_4$alkyl or phenyl-$C_1$–$C_4$alkoxy;

with the proviso that 3-diethylamino-7-methylsulfonylfluoran, 3-diethylamino-7-nitrofluoran, 3-diethylamino-6-methyl-7-nitrofluoran, 3-diethylamino-7-formylfluoran, and 3-diethylaminofluoran-7-sulfonic acid are not comprised.

Preferred compounds of formula I are those wherein $R_1$ is hydrogen or $C_1$–$C_4$alkyl;

$R_2$ and $R_3$ are each independently of the other hydrogen; $C_1$–$C_5$alkyl; or $R_2$ and $R_3$ together with the linking nitrogen atom are an unsubstituted or $C_1$–$C_4$alkyl-substituted pyrrolidino or piperidino ring;

$R_4$ is hydrogen or $C_1$–$C_4$alkyl;

$R_5$ is nitro; $SO_2R_7$; $SO_2OR_8$; $SO_2NR_9R_{10}$; $COR_{11}$; $CONR_9R_{10}$; or $C_1$–$C_4$haloalkyl;

n is 0; 1; 2; 3; or 4;

$R_6$ is halogen when n is 1, 2, 3 or 4; or is $C_1$–$C_4$alkyl or $C_1$–$C_4$haloalkyl when n is 1 or 2; or, when n is 1, is nitro, $COR_{11}$, amino, mono-$C_1$–$C_4$alkylamino or di-$C_1$–$C_4$alkylamino;

$R_7$ is $C_1$–$C_4$alkyl; or $C_1$–$C_4$haloalkyl; unsubstituted phenyl or phenyl-$C_1$–$C_2$alkyl; phenyl or phenyl-$C_1$–$C_2$alkyl which is substituted by halogen, $C_1$–$C_4$alkyl, $C_1$–$C_4$haloalkyl or $C_1$–$C_4$alkoxy;

$R_8$ is hydrogen, $C_1$–$C_4$alkyl; $C_1$–$C_4$haloalkyl; unsubstituted phenyl or phenyl-$C_1$–$C_2$alkyl; or phenyl or phenyl-$C_1$–$C_2$alkyl which is substituted by halogen, $C_1$–$C_4$alkyl, $C_1$–$C_4$haloalkyl or $C_1$–$C_4$alkoxy;

$R_9$ and $R_{10}$ are each independently of the other hydrogen; or $C_1$–$C_4$alkyl;

$R_9$ and $R_{10}$ together with the linking nitrogen atom are an unsubstituted or a $C_1$–$C_4$alkyl-substituted pyrrolidino or piperidino ring; and $R_{11}$ is hydrogen; $C_1$–$C_4$alkyl; $C_1$–$C_4$haloalkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy.

Particularly preferred fluorans of formula I are those wherein $R_1$ is hydrogen or $C_1$–$C_4$alkyl;

$R_2$ and $R_3$ are each independently of the other hydrogen; $C_1$–$C_5$alkyl; or $R_2$ and $R_3$ together with the linking nitrogen atom are an unsubstituted pyrrolidino or piperidino ring;

$R_4$ is hydrogen or $C_1$–$C_4$alkyl;

$R_5$ is nitro; $SO_2R_7$; $SO_2NR_9R_{10}$; $COR_{11}$; $CONR_9R_{10}$; or $C_1$–$C_4$-haloalkyl;

n is 0, 1, 2, 3 or 4;

$R_6$ is halogen when n is 1, 2, 3 or 4,; is nitro, $C_1$–$C_4$alkyl, $C_1$–$C_4$haloalkyl when n is 1 or 2; or, when n is 1, is $COR_{11}$, amino, mono-$C_1$–$C_4$alkylamino or di-$C_1$–$C_4$alkylamino;

$R_7$ is $C_1$–$C_4$alkyl; or $C_1$–$C_4$haloalkyl; unsubstituted phenyl or phenyl-$C_1$–$C_2$alkyl; phenyl or phenyl-$C_1$–$C_2$alkyl which is substituted by halogen, $C_1$–$C_4$alkyl, $C_1$–$C_4$haloalkyl or $C_1$–$C_4$alkoxy;

$R_8$ is hydrogen, $C_1$–$C_4$alkyl; $C_1$–$C_4$haloalkyl; unsubstituted phenyl or phenyl-$C_1$–$C_2$alkyl; or phenyl or phenyl-$C_1$–$C_2$alkyl which is substituted by halogen, $C_1$–$C_4$alkyl, $C_1$–$C_4$haloalkyl or $C_1$–$C_4$alkoxy;

$R_9$ and $R_{10}$ are each independently of the other hydrogen or $C_1$–$C_4$alkyl;

$R_9$ and $R_{10}$ together with the linking nitrogen atom are an unsubstituted or a $C_1$–$C_4$alkyl-substituted pyrrolidino or piperidino ring; and $R_{11}$ is hydrogen; $C_1$–$C_4$alkyl; $C_1$–$C_4$haloalkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy.

To be singled out for special mention are fluorans of formula I, wherein $R_1$ is hydrogen or methyl;

$R_2$ and $R_3$ are each independently of the other hydrogen; $C_1$–$C_5$alkyl; or $R_2$ and $R_3$ together with the linking nitrogen atom are an unsubstituted pyrrolidino or piperidino ring;

$R_4$ is hydrogen or methyl;

$R_5$ is nitro; $SO_2R_7$; $SO_2NR_9R_{10}$; $COR_{11}$; $CONR_9R_{10}$; or $C_1$–$C_4$-haloalkyl;

n is 0, 1, 2, 3 or 4;

$R_6$ is halogen when n is 1, 2, 3 or 4; is nitro or methyl when n is 1 or 2; or, when n is 1, nitro, amino, mono-$C_1$–$C_4$alkylamino or di-$C_1$–$C_4$alkylamino;

$R_7$ is $C_1$–$C_4$alkyl; or $C_1$–$C_4$haloalkyl; unsubstituted phenyl or phenyl which is substituted by halogen, $C_1$–$C_4$alkyl or $C_1$–$C_4$alkoxy;

$R_9$ and $R_{10}$ are each independently of the other hydrogen or $C_1$–$C_4$alkyl;

$R_{11}$ is hydrogen; $C_1$–$C_4$alkyl; $C_1$–$C_4$alkoxy; unsubstituted phenyl or phenyl which is substituted by halogen, $C_1$–$C_4$alkyl, $C_1$–$C_4$haloalkyl or $C_1$–$C_4$alkoxy; phenyl-$C_1$–$C_2$alkyl or phenyl-$C_1$–$C_2$alkoxy.

In particular, the invention relates to colour former systems of formula I, of preferred formula I and of particularly preferred formula I, wherein $R_5$ is $SO_2R_7$, $SO_2OR_8$, $SO_2NR_9R_{10}$, $COR_{11}$, $CONR_9R_{10}$, $C_1$–$C_4$-haloalkyl or nitro, and $R_2$ $R_3$ are each independently of the other hydrogen or $C_4$–$C_8$alkyl;

$R_2$ and $R_3$ together with the linking nitrogen atom are an unsubstituted or $C_1$–$C_4$alkyl-substituted pyrrolidino, piperidino, morpholino, thiomorpholino or piperazino ring.

Among these compounds of formula I, those compounds are preferred in which $R_5$ is $COR_{11}$ and, most particularly, those in which $R_{11}$ is $C_1$-$C_4$alkyl, $C_1$-$C_4$alkoxy or phenyl-$C_1$-$C_4$alkoxy. Compounds of preeminent interest are those in which $R_{11}$ is $C_1$-$C_4$alkoxy or phenyl-$C_1$-$C_4$alkoxy.

The compounds of formula I can be prepared by per se known processes. The invention also relates to a process for the preparation of compounds of formula I, which comprises a) reacting a benzophenone of formula II with a phenol or phenol ether of formula III

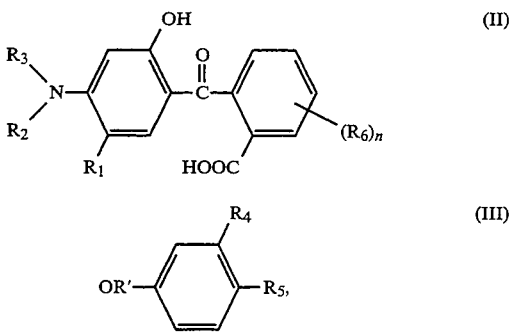

wherein $R_1$ to $R_6$ and n are as previously defined and R' is hydrogen or $C_1$-$C_4$alkyl, in the preferred temperature range from 0° to 70° C., in 50 to 100% sulfuric acid, to a phthalide of formula IV

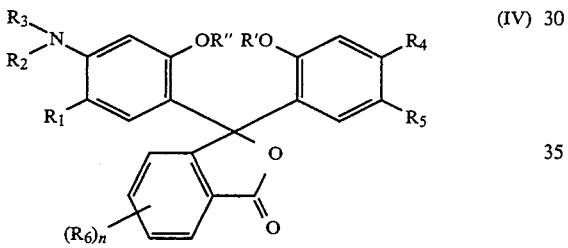

and subsequent cyclisation in the temperature range from 20° to 100° C. to a compound of formula I.

Some of the starting compounds of formulae (II) and (VIII) are known from the literature or can be prepared by methods analogous to known ones. Thus, for example, suitable compounds of formula (III) are disclosed in DE-A-4 029 131 or U.S. Pat. No. 1,939,416. Processes for their preparation are also described in Houben Weyl, Methoden der organisthen Chemic Vol. IX, p. 231 et seq.

Compounds of formula I can also be prepared by derivatisation reactions from other compounds of formula I.

Thus, for example, the sulfones or the sulfonamides of formula I ($R_5$=$SO_2R_7$ or $SO_2NR_9R_{10}$) are prepared by reacting the sulfone esters of formula I ($R_5$=$SO_2OR_8$) with carbanions or Grignard reagents ($R_7$- or $RTMg$-halogen) or amines ($HNR_9R_{10}$).

Hence the invention further relates to a process for the preparation of sulfones of formula I, wherein
$R_5$ is $SO_2R_7$,
which comprises reacting a sulfone ester of formula I, wherein
$R_5$ is $SO_2OR_8$,
with a carbanion or Grignard reagent of the general formula V

$R_7$- $M^+$ or $R_7Mg$-Hal (V), wherein
$M^+$ is a cation equivalent of an alkali metal or alkaline earth metal ion; and
Hal is halogen,
and
$R_7$ is as previously defined,
and
a process for the preparation of sulfonamides of formula I, wherein
$R_5$ is $SO_2NR_9R_{10}$,
which comprises reacting a sulfone ester of formula I, wherein
$R_5$ is $SO_2OR_8$,
with an amine of formula VI

HNR$_9$R$_{10}$ (VI), wherein
$R_9$ and $R_{10}$ are as previously defined.

The invention is illustrated by the following Examples in which percentages are by weight unless otherwise indicated.

PREPARATION OF THE FLUORANS OF FORMULA I

EXAMPLE 1: 3-Diethylamino-7-butylsulfonylfluoran 14.5 g of 1-ethoxy-4(butylsulfonyl)benzene are added over 30 minutes at 15°–30° C. to 18.8 g of 4'-diethylamino-2'-hydroxybenzophenone-2-carboxylic acid in 120 ml of 98% sulfuric acid and the mixture is stirred for 24 hours at 20°–25° C. The reaction mixture is then charged to a mixture of 510 ml of 40% aqueous sodium hydroxide, 550 ml of water and 250 ml of toluene, whereupon a final temperature of 83° C. is reached. The batch is stirred for 1 hour at 80°–83° C. The toluene phase is separated and washed with 2×200 ml of water. The toluene is removed by distillation and 29.1 g of the title compound are isolated and purified by recrystallisation from isopropanol, giving colourless crystals of the purified compound of formula

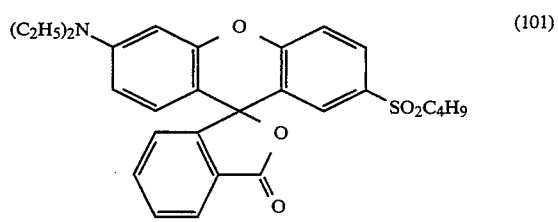

Melting point: 134°–136° C.

The compound develops an orange image on commercial CF papers. No migration from CB papers (capsules) can be observed.

EXAMPLE 2:
3-Diethylamino-7-p-tolylsulfonylfluoran 1.3 g of 4'-diethylamino-2'-hydroxybenzophenone-2-carboxylic acid are dissolved in 200 ml of 98% sulfuric acid at 34°–40° C. Then 24.8 g of 4-hydroxy-4'-methyl-diphenylsulfone are added in increments at 30° C. and the mixture is stirred for 20 hours at 20°–25° C. The red solution obtained is poured onto 1000 g of ice/water and the readily filterable residue is isolated. The filter product is washed with water, taken up in 200 ml of 4% aqueous sodium hydroxide and 600 ml of toluene, and the solution is stirred for 1 hour at 85° C. The toluene phase is separated, washed with 2×100 ml of warm water and concentrated by distillation until the product crystallises. After cooling, the crystals are washed with a small amount of isopropanol and dried, giving 27.2 g of colourless crystals of the compound of formula

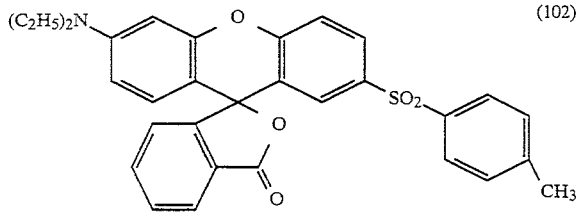
(102)

Melting point: 221°–222° C.

The compound develops an orange image on activated clay.

EXAMPLE 3

3-Diethylamino-7-ethoxycarbonylfluoran a. via the acid 313 g of 4'-diethylamino-2'-hydroxybenzophenone-2-carboxylic acid are dissolved at c. 40° C. in 830 g of 98% sulfuric acid. Then 138 g of 4-hydroxybenzoic acid are added over c. 30 minutes and the temperature is raised to 80° C. and the mixture is kept for 4 hours at this temperature. The condensation solution is poured into 2000 ml of water/ice over c. 2 hours, while keeping the pH between 1 and 4 by the simultaneous addition of c. 1500 ml of 10 N aqueous sodium hydroxide. The temperature is kept at a maximum of 35° C. by the addition of ice. The volume is 4500 ml. The suspension is filtered after 1 hour at 30° C. and the filter product is washed with c. 3l of water of 30° C., giving 1600 g of a moist intermediate of formula

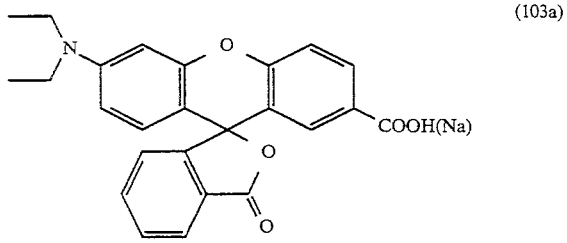
(103a)

which has a weight of 440 g after drying. 1500 g of the moist intermediate (103a) are suspended at c. 70° C. in 200 ml of toluene and 5 g of tetrabutylammonium bromide. The suspension is cooled to 40° C. and 308 g of diethyl sulfate are added. With efficient stirring, the temperature is kept for 3 hours at 40° to 45° C., while keeping the pH at c. 11 with aqueous sodium hydroxide. The batch is heated to 70° C. and thereafter kept for 1 hour at 70°–75° C. The phases are then separated. The toluene phase is washed with water and subsequently 700 ml of toluene are distilled off under reduced pressure. The residue is filtered over activated carbon and 500 ml of methanol are added at 60° C. The product crystallises completely after stirring at low temperature: The crystalline product is isolated by filtration, washed with 400 ml of methanol and dried, giving 236.5 g of the colourless product of formula

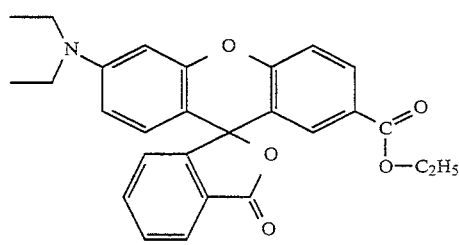
(103)

Melting point: 151°–153° C.

The product has excellent solubility in the commercially available capsule oils, exhibits no migration from the capsules, and develops a deep orange image on commercial CF papers as well as in thermoapplication.

b. Direct synthesis 31.3 g of 4'-diethylamino-2'-hydroxybenzophenone-2-carboxylic acid are dissolved at 35°–40° C. in 45 ml of 100% of sulfuric acid (monohydrate). The solution is cooled to 10° C. and then 16.6 g of ethyl 4-hydroxybenzoate are added over 30 minutes. The mixture is allowed to warm to 23° C. and stirred for 20 hours at 23°–28° C. The reaction mass is poured into 800 ml of ice/water and filtered after 1 hour at 22° C. The filter product is washed with 500 ml of water, giving 93 g of a moist product of formula (103), which is partially in the form of the phthalide.

The filter cake is then slurried in 800 ml of toluene, 21.4 g of sodium carbonate are added and the batch is stirred at 75° C. for 15 minutes. The water is distilled off as an azeotrope under reduced pressure, and the toluene solution is filtered and concentrated to dryness, giving 28.6 g of a crude product of formula (103) which, after recrystallisation, has a melting point of 151°–153° C. and the same properties as the product prepared in 3a.

EXAMPLE 4

7.8 g 4'-Diethylamino-2'-hydroxybenzophenone-2-carboxylic acid are dissolved at 35° C. in 50 ml of 98% sulfuric acid. Then 8.9 g of 2-(4,6-diphenyl-1,3,5-triazin-2-yl)-5methoxyphenol are added at 20°–25° C. and the mixture is stirred for 24 hours at 20°–25° C. The solution is charged at 80° C. to a mixture of 230 ml of water, 210 ml of 10 N of aqueous sodium hydroxide and 550 ml of toluene and the batch is stirred for 30 minutes at 80°–85° C. The aqueous phase is separated, washed with warm water, and the filtered and clarified toluene solution is cooled, with stirring. After 2 hours the batch is filtered at 20° C. and the filter product is dried, giving 12 g of colourless crystals of formula

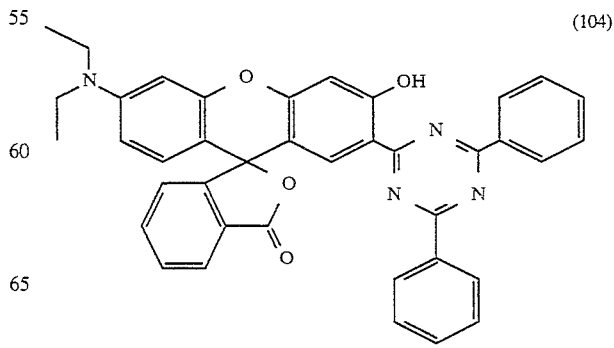
(104)

Melting point: >270° C.

This compound develops a red image of good lightfastness on commercial CF paper.

EXAMPLE 5

800 g of moist filter cake of formula (103a) are slurried in 10 N aqueous sodium hydroxide and 1 g of Aliquat 336. The slurry is heated to 85° C. and 80 ml of benzyl bromide are added dropwise to the resultant solution (pH 10.5) at 85°–89° C. over 1 hour. This temperature is kept for a further 4 hours, then lowered to 80° C. Then 500 ml of toluene are added and the aqueous phase is separated. The toluene phase is washed with 2×100 ml of water, clarified by filtration, dried and stirred cold, whereupon 111.4 g of the colourless product of formula

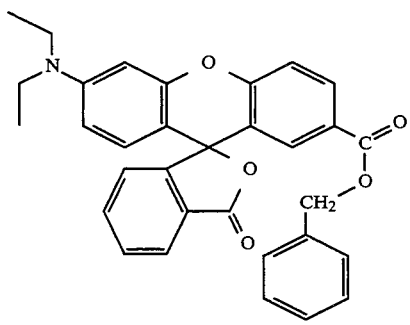
(105)

crystallise out.

Melting point: 108°–110° C.

This colour former has excellent solubility in capsule oils, does not sublime, and develops a deep orange image on commercial CF papers.

EXAMPLE 6

64 g of moist filter cake of formula (103a) are stirred for 1 hour at 20°–25° C. in 0.1 g of Aliquat 336, 4 ml of 10 N aqueous sodium hydroxide and. 8 ml of propyl bromide. Then a further 4 ml of sodium hydroxide solution are added and the reaction mixture is heated with efficient stirring to 80° C. This temperature is kept for 1 hour, 200 ml of toluene are added and the aqueous phase is separated. The toluene phase is washed with 3×50 ml of water and concentrated, giving 15.4 g of crude product of formula

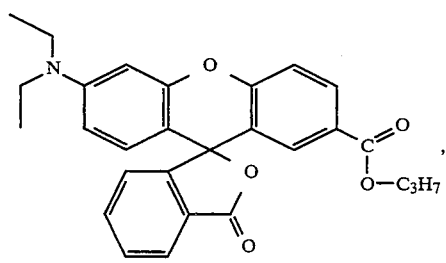
(106)

which, after recrystallisation from isopropyl alcohol, has a melting point of 110°–112° C.

This colour former has excellent solubility in capsule oils, does not sublime, and develops an orange image on commercial CF papers.

EXAMPLE 7

12.5 g of 4'-diethylamino-2'-hydroxybenzophenone-2-carboxylic acid are dissolved at a maximum temperature of 40° C. in 30 ml of 98% sulfuric acid. Then 9.1 g of 2,4-dihydroxybenzophenone are added at 20°–25° C. and, after 18 hours, the reaction mass is charged to 300 ml of ice/water. The precipitate is isolated by filtration at 20° C. and washed with 300 ml of water, giving 38 g of a moist product, which is charged to 50 ml of toluene and 50 ml of 1 N sodium hydroxide solution. The emulsion is heated to 80° C. and, after keeping this temperature for 1 hour, worked up as follows: the aqueous phase is separated, the toluene phase is washed with 3×100 ml of water of 50° C. and the combined aqueous phases are adjusted with 10 N hydrochloric acid to pH 7, whereupon the product precipitates. The product is isolated by filtration and dried, giving 11.65 g of the product of formula

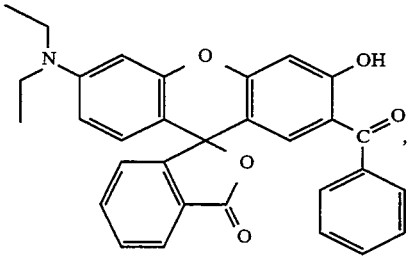
(107)

which, after recrystallisation from 300 ml of toluene/isopropyl alcohol in the ratio 1: 1 has a melting point of 201°–202° C. This colour former develops on a deep red image of good lightfastness on commercial CF papers.

The compounds of Table 1 can be prepared by procedures similar to those described in the foregoing Examples.

TABLE 1

Compounds of formula

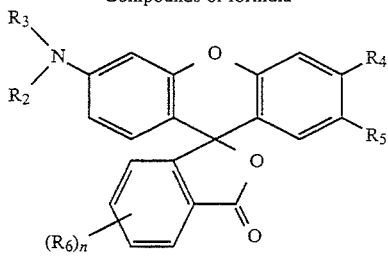

| Cmpd. No | $R_1$ | $R_2$ | $R_3$ | $R_4$ | $R_5$ | $R_6$ | mp [°C.] |
|---|---|---|---|---|---|---|---|
| (108) | H | $C_2H_5$ | H | H | $COOC_2H_5$ | n = 0 | 197-8 |
| (109) | H | n-$C_4H_9$ | n-$C_4H_9$ | H | 4-($CH_3$)$C_6H_4$-$SO_2$- | n = 0 | 70*) |
| (110) | H | $CH_3$ | $CH_3$ | H | $SO_2$—$CH_3$ | n = 0 | 257-8 |
| (111) | $CH_3$ | $CH_3$ | $CH_3$ | H | $SO_2C_2H_5$ | n = 0 | |
| (112) | H | $C_2H_5$ | $C_2H_5$ | H | $SO_2NHC_4H_9$ | n = 0 | 95-102 |
| (113) | H | $C_2H_5$ | $C_2H_5$ | H | $SO_2N(C_4H_9)_2$ | n = 0 | *) |
| (114) | H | n-$C_4H_9$ | n-$C_4H_9$ | H | $NO_2$ | n = 0 | 184 |
| (115) | H | $C_2H_5$ | $C_2H_5$ | H | $SO_2C_2H_5$ | n = 0 | 180-4 |
| (116) | H | $C_2H_5$ | $C_2H_5$ | H | $SO_2CH_2CH(CH_3)_2$ | n = 0 | 108 |
| (117) | H | n-$C_4H_9$ | n-$C_4H_9$ | H | $CONH_2$ | n = 0 | 248-9 |
| (118) | H | $C_2H_5$ | $C_2H_5$ | H | $SO_2C_3H_7$ | n = 0 | 152-3 |
| (119) | H | $C_2H_5$ | $C_2H_5$ | H | $CO$—$C_6H_5$ | n = 0 | oil |
| (120) | H | $C_2H_5$ | $C_2H_5$ | H | $C_6H_5CH_2$- | n = 0 | 130-2 |
| (121) | H | cyclohexyl | $CH_3$ | H | $COOC_2H_5$ | n = 0 | |
| (122) | H | cyclohexyl | H | H | $COOC_2H_5$ | n = 0 | |
| (123) | H | $C_2H_5$ | H | H | $COOC_2H_5$ | n = 0 | |
| (124) | H | $C_4H_9$ | H | H | $COOC_2H_5$ | n = 0 | |
| (125) | H | 4-($CH_3$)$C_6H_4$- | $C_2H_5$ | H | $COOC_2H_5$ | n = 0 | |
| (126) | $CH_3$ | $C_2H_5$ | H | H | $COOC_2H_5$ | n = 0 | |

TABLE 1-continued

Compounds of formula

| Cmpd. No | R₁ | R₂ | R₃ | R₄ | R₅ | R₆ | mp [°C.] |
|---|---|---|---|---|---|---|---|
| (127) | H | (tetrahydrofurfuryl)-CH₂— | C₂H₅ | H | COOC₂H₅ | n = 0 | |
| (128) | H | CH₃-CH(CH₂)₂— with CH₃ | C₂H₅ | H | COOC₂H₅ | n = 0 | |
| (129) | H | (CH₃)₂CH—CH₂— | C₂H₅ | H | COOC₂H₅ | n = 0 | |
| (130) | H | n-C₆H₁₃ | C₂H₅ | H | COOC₂H₅ | n = 0 | |
| (131) | H | n-C₅H₁₁ | n-C₅H₁₁ | H | COOC₂H₅ | n = 0 | |
| (132) | H | C₆H₅ | C₆H₅ | H | COOC₂H₅ | n = 0 | |
| (133) | CH₃ | C₂H₅ | H | H | COOC₂H₅ | —C(CH₃)₃ (pos. 5' or 6') | |
| (134) | H | pyrrolidino | H | H | COOC₂H₅ | —C(CH₃)₃ (pos. 5'6') | |
| (135) | CH₃ | n-C₄H₉ | H | H | COOC₂H₅ | n = 0 | |
| (136) | CH₃ | C₆H₅—CH₂— | H | H | COOC₂H₅ | n = 0 | |
| (137) | CH₃ | CH₃ | CH₃ | H | COOC₂H₅ | n = 0 | |
| (138) | CH₃ | CH₃ | CH₃ | H | COOC₂H₅ | Cl* | |
| (139) | H | C₂H₅ | C₂H₅ | H | COOC₂H₅ | Cl (pos. 4',5',6',7') | |
| (140) | H | H₃C-CH(CH₂-O-)N-C₂H₅ (morpholino derivative) | | H | COOC₂H₅ | n = 0 | |
| (141) | H | C₂H₅ | C₂H₅ | H | COOC₂H₅ | COOC₂H₅ (pos. 5' or 6') | |
| (142) | H | (CH₃)₂CH— | CH₃ | H | COOC₂H₅ | n = 0 | |

TABLE 1-continued

Compounds of formula

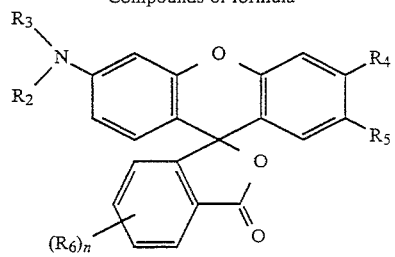

| Cmpd. No | $R_1$ | $R_2$ | $R_3$ | $R_4$ | $R_5$ | $R_6$ | mp [°C.] |
|---|---|---|---|---|---|---|---|
| (143) | H | CH(CH$_3$)CH$_2$— with CH$_3$ | CH$_3$ | H | COOC$_2$H$_5$ | n = 0 | |
| (144) | H | C$_2$H$_5$ | CH$_3$ | H | COOC$_2$H$_5$ | n = 0 | |
| (145) | H | $R_2$ und $R_3$ = CH$_3$CHCH$_2$— with CH$_3$ | | H | COOC$_2$H$_5$ | n = 0 | |
| (146) | H | CH$_2$=CHCH$_2$— | CH$_3$OC$_2$H$_4$ | H | COOC$_2$H$_5$ | n = 0 | |
| (147) | H | CH$_2$=CHCH$_2$— | C$_2$H$_5$OC$_2$H$_4$— | H | COOC$_2$H$_5$ | n = 0 | |
| (148) | H | CH(CH$_3$)CH$_2$— with CH$_3$ | CH$_3$OC$_2$H$_4$ | H | COOC$_2$H$_5$ | n = 0 | |
| (149) | H | CH(CH$_3$)CH$_2$— with CH$_3$ | C$_2$H$_5$OC$_2$H$_4$— | H | COOC$_2$H$_5$ | n = 0 | |
| (150) | H | CH(CH$_3$)CH$_2$— with CH$_3$ | C$_2$H$_5$OC$_2$H$_4$— | H | COOC$_2$H$_5$ | n = 0 | |
| (151) | H | cyclohexyl | n-C$_3$H$_7$ | H | COOC$_2$H$_5$ | n = 0 | |
| (152) | H | cyclohexyl | n-C$_4$H$_9$ | H | COOC$_2$H$_5$ | n = 0 | |
| (153) | H | cyclohexyl | H$_2$C=CHCH$_2$— | H | COOC$_2$H$_5$ | n = 0 | |
| (154) | H | $R_2$ und $R_3$ = H$_2$C=CHCH$_2$— with CH$_3$ | | H | COOC$_2$H$_5$ | n = 0 | |
| (155) | H | H$_2$C=CHCH$_2$— | n-C$_4$H$_9$ | H | COOC$_2$H$_5$ | n = 0 | |
| (156) | H | H$_2$C=CHCH$_2$— | CH(CH$_3$)CH$_2$— | H | COOC$_2$H$_5$ | n = 0 | |
| (157) | H | n-C$_4$H$_9$ | CH$_3$CH$_2$CH— with CH$_3$ | H | COOC$_2$H$_5$ | n = 0 | |

TABLE 1-continued

Compounds of formula

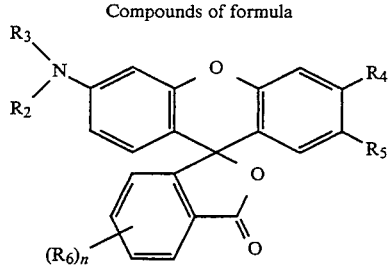

| Cmpd. No | R₁ | R₂ | R₃ | R₄ | R₅ | R₆ | mp [°C.] |
|---|---|---|---|---|---|---|---|
| (158) | H | n-C₅H₁₁ | CH₃—CH₂—CH(CH₃)— | H | COOC₂H₅ | n = 0 | |
| (159) | H | CH₃ | CH₃—CH₂—CH(CH₃)— | H | COOC₂H₅ | n = 0 | |
| (160) | H | n-C₃H₇ | CH₃—CH₂—CH(CH₃)— | H | COOC₂H₅ | n = 0 | |
| (161) | H | | R₂ und R₃ = CH₃CH₂CH(CH₃)CH₂— | H | COOC₂H₅ | n = 0 | |

USE EXAMPLE 1

Preparation of a pressure-sensitive copying paper

A solution of 1 g of the fluoran of formula (101) (Example 1) in 80 g of diisopropylnaphthalene and 19 g of kerosene is encapsulated by coacervation in a manner known per se with gelatin and gum arabic. The microcapsules are mixed with starch solution and coated on a sheet of paper. The face of a second sheet of paper is coated with activated clay as colour developer. The first sheet containing the colour former and the sheet coated with the developer are laid on top of each other with the coated sides face to face. Pressure is exerted on the first sheet by handwriting or by typewriter and a deep orange copy of excellent lightfastness develops immediately on the sheet coated with the developer.

USE EXAMPLE 2

Preparation of a pressure-sensitive copying paper for black copies

The procedure of Use Example 1 is repeated, except that the fluoran of formula (101) is replaced with a mixture of 1 of the compound of formula (103)
0.8 g of 3,3-bis(4-dimethylaminophenyl)-6-dimethylaminoisobenzofuran-3H-1-one
0.8 of N-butylcarbazol-3-yl-bis(4-N-methyl-N-phenylaminophenyl)methane
2.4 g of 3-diethylamino-7-dibenzylaminofluoran
to give a pressure-sensitive recording material which is fast to sublimation and which gives a deep, lightfast black copy when pressure is exerted by writing by hand or typewriter.

USE EXAMPLE 3

Sublimation/migration test

The black copying paper obtained according to Example 2 is tested for fastness to sublimation and migration as follows:

The face of a sheet of paper coated with activated clay as colour developer (CF sheet) is contacted with a sheet (CB sheet) which is coated with the microencapsulated formulation of the mixture of Use Example 2 for producing black copies. A specimen of writing is produced with a word processor (Olitex 20) in the centre of the test area. Afterwards the top- and underside are each covered with 5 (untreated) base papers. The packets so obtained are weighted with an aluminium plate (c. 1 kg) and kept for 5 hours at 110° C. in a drying oven. The sheet is subsequently assessed as follows:

CF sheet:
  discolouration
  staining (migration)
writing:
  change of shade
  loss of intensity
  staining In this test the test papers exhibited a marked enhancement of the fastness to sublimation and migration compared with known black mixtures.

USE EXAMPLE 4

Preparation of a heat-sensitive recording material

In a ball mill, 32 g of 4,4'-isopropylidenediphenol (bisphenol A), 3.8 g of the distearylamide of ethylenediamine, 39 g of kaolin, 20 g of an 88% hydrolysed polyvinyl alcohol and 500 ml of water are milled to a particle size of c. 5 μm. In a second ball mill, 6 g of the compound of formula (103) obtained in Example 3, 3 g of 88% hydrolysed polyvinyl alcohol and 60 ml of water are milled to a particle size of c. 3 μm.

Both dispersions are mixed and coated to a dry coating weight of 5.5 g/m² on a sheet of paper. A deep orange image of excellent lightfastness is produced by contacting the paper with a heated metal stylus. The paper has no background discolouration.

USE EXAMPLE 5

Preparation of a heat-sensitive recording material for black copies

In accordance with the general procedure described in Example 4, a heat-sensitive recording material for black copies is prepared by replacing the 6.0 g of the compound of formula (103) with a mixture comprising 3 g of the compound of formula (103) and 3 g of 3-diethylamino-7-dibenzylaminofluoran.

When using a commercially available facsimile machine (Infotec 6510), black writing develops on the dried paper.

What is claimed is:

1. A pressure-sensitive or heat-sensitive recording material comprising at least one colour former of formula (I)

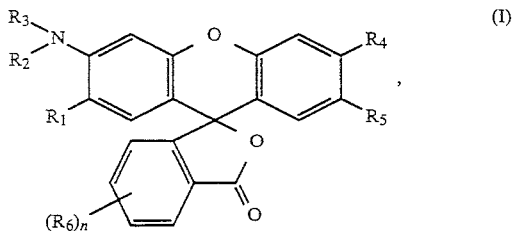

wherein $R_1$ is hydrogen or $C_1$-$C_4$alkyl;

$R_2$ and $R_3$ are each independently of the other hydrogen; $C_1$-$C_8$alkyl; unsubstituted or $C_1$-$C_4$alkyl-halogen-substituted $C_4$-$C_7$cycloalkyl; unsubstituted phenyl or phenyl which is substituted by $C_1$-$C_4$alkyl, hydroxy or halogen; phenyl-$C_1$-$C_4$alkyl; $C_3$-$C_6$alkenyl; $C_1$-$C_4$alkoxy; $C_1$-$C_4$alkoxy-$C_1$-$C_4$alkyl; 2-tetrahydrofuranyl, or $R_2$ and $R_3$ together with the linking nitrogen atom are an unsubstituted or $C_1$-$C_4$alkyl-substituted pyrrolidino, piperidino, morpholino, thiomorpholino or piperazino ring;

$R_4$ is hydrogen, hydroxy or $C_1$-$C_4$alkyl;

$R_5$ is $COR_{11}$; $CONR_9R_{10}$;

$R_6$ is halogen; nitro; $C_1$-$C_4$alkyl; $C_1$-$C_4$haloalkyl; amino; mono-$C_1$-$C_4$alkylamino; di-$C_1$-$C_4$alkylamino; or $COR_{11}$;

n is 0; 1; 2; 3; or 4;

$R_9$ and $R_{10}$ are each independently of the other hydrogen; or $C_1$-$C_8$alkyl; or $R_9$ and $R_{10}$ together with the linking nitrogen atom are an unsubstituted or a $C_1$-$C_4$alkyl-substituted pyrrolidino, piperidino, morpholino, thiomorpholino or piperazino ring; and $R_{11}$ is $C_1$-$C_8$alkyl; $C_1$-$C_8$alkoxy; $C_1$-$C_8$haloalkyl; phenyl which is substituted by halogen, $C_1$-$C_4$haloalkyl, or $C_1$-$C_4$alkoxy; phenyl-$C_1$-$C_4$alkyl or phenyl-$C_1$-$C_4$alkoxy;

with the proviso that 3-diethylaminofluoran-7-carboxymethylester is not comprised.

2. A recording material according to claim 1, comprising at least one colour former of formula (I), wherein $R_1$ is hydrogen or $C_1$-$C_4$alkyl;

$R_2$ and $R_3$ are each independently of the other hydrogen; $C_1$-$C_5$alkyl; or $R_2$ and $R_3$ together with the linking nitrogen atom are an unsubstituted or $C_1$-$C_4$alkyl-substituted pyrrolidino or piperidino ring;

$R_4$ is hydrogen or $C_1$-$C_4$alkyl;

$R_5$ is $COR_{11}$; $CONR_9R_{10}$;

n is 0; 1; 2; 3; or 4;

$R_6$ is halogen when n is 1, 2, 3 or 4; $C_1$-$C_4$alkyl or $C_1$-$C_4$haloalkyl when n is 1 or 2; or, when n is 1, nitro, $COR_{11}$, amino, mono-$C_1$-$C_4$alkylamino or di-$C_1$-$C_4$alkylamino;

$R_9$ and $R_{10}$ are each independently of the other hydrogen; or $C_1$-$C_4$alkyl;

$R_9$ and $R_{10}$ together with the linking nitrogen atom are an unsubstituted or a $C_1$-$C_4$alkyl-substituted pyrrolidino or piperidino ring; and $R_{11}$ is $C_1$-$C_4$alkyl; $C_1$-$C_4$haloalkyl; $C_1$-$C_4$alkoxy; phenyl which is substituted by halogen, $C_1$-$C_4$haloalkyl or $C_1$-$C_4$alkoxy; phenyl-$C_1$-$C_2$alkyl or phenyl-$C_1$-$C_2$alkoxy.

3. A recording material according to claim 1 comprising at least one colour former of formula I wherein $R_1$ is hydrogen or methyl;

$R_2$ and $R_3$ are each independently of the other hydrogen; $C_1$-$C_5$alkyl; or $R_2$ and $R_3$ together with the linking nitrogen atom are an unsubstituted pyrrolidino or piperidino ring;

$R_4$ is hydrogen or methyl;

$R_5$ is $COR_{11}$; $CONR_9R_{10}$;

n is 0, 1, 2, 3 or 4;

$R_6$ is halogen when n is 1, 2, 3 or 4; or is methyl when n is 1 or 2; or, when n is 1, is nitro, amino, mono-$C_1$-$C_4$alkylamino or di-$C_1$-$C_4$alkylamino;

$R_9$ and $R_{10}$ are each independently of the other hydrogen or $C_1$-$C_4$alkyl;

$R_{11}$ is $C_1$-$C_4$alkyl; $C_1$-$C_4$alkoxy; phenyl which is substituted by halogen, $C_1$-$C_4$haloalkyl or $C_1$-$C_4$alkoxy; phenyl-$C_1$-$C_2$alkyl or phenyl-$C_1$-$C_2$alkoxy.

4. A recording material according to claim 1 comprising at least one colour former of formula (I), wherein $R_5$ is $COR_{11}$.

5. A recording material according to claim 4, comprising at least one colour former of formula (I), wherein $R_{11}$ is $C_1$-$C_4$alkyl, $C_1$-$C_4$alkoxy or phenyl-$C_1$-$C_2$alkoxy.

6. A recording material according to claim 4, wherein $R_{11}$ is $C_1$-$C_4$alkoxy or phenyl-$C_1$-$C_2$alkoxy.

7. A recording material according to claim 1 comprising at least one colour former of formula (I), wherein $R_5$ is $CONR_9R_{10}$.

8. A fluoran of general formula (I)

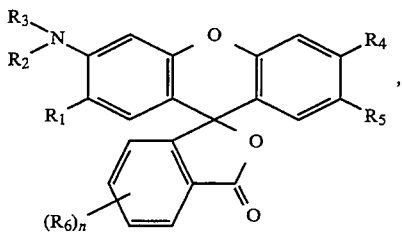

wherein $R_1$ is hydrogen or $C_1$–$C_4$alkyl;

$R_2$ and $R_3$ are each independently of the other hydrogen; $C_1$–$C_8$alkyl; unsubstituted or $C_1$–$C_4$alkyl-halogen-substituted $C_4$–$C_7$cycloalkyl; unsubstituted phenyl or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$–$C_4$alkyl; 2-tetrahydrofuranyl, or $R_2$ and $R_3$ together with the linking nitrogen atom are an unsubstituted or $C_1$–$C_4$alkyl-substituted pyrrolidino, piperidino, morpholino, thiomorpholino or piperazino ring;

$R_4$ is hydrogen, hydroxy or $C_1$–$C_4$alkyl;

$R_5$ is $COR_{11}$; $CONR_9R_{10}$;

$R_6$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_{11}$;

n is 0; 1; 2; 3; or 4;

$R_9$ and $R_{10}$ are each independently of the other hydrogen; or $C_1$–$C_8$alkyl; or $R_9$ and $R_{10}$ together with the linking nitrogen atom are an unsubstituted or a $C_1$–$C_4$alkyl-substituted pyrrolidino, piperidino, morpholino, thiomorpholino or piperazino ring; and $R_{11}$ is $C_1$–$C_8$alkyl; $C_1$–$C_8$alkoxy; $C_1$–$C_8$haloalkyl; phenyl which is substituted by halogen, $C_1$–$C_4$haloalkyl, or $C_1$–$C_4$alkoxy; or phenyl-$C_1$–$C_4$alkyl or phenyl-$C_1$–$C_4$alkoxy;

with the proviso that 3-diethylaminofluoran-7-carboxymethylester is not comprised.

9. A fluoran according to claim 8, wherein $R_1$ is hydrogen or $C_1$–$C_4$alkyl;

$R_2$ and $R_3$ are each independently of the other hydrogen; $C_1$–$C_5$alkyl; or $R_2$ and $R_3$ together with the linking nitrogen atom are an unsubstituted or $C_1$–$C_4$alkyl-substituted pyrrolidino or piperidino ring;

$R_4$ is hydrogen or $C_1$–$C_4$alkyl;

$R_5$ is $COR_{11}$; $CONR_9R_{10}$;

n is 0; 1; 2; 3; or 4;

$R_6$ is halogen when n is 1, 2, 3 or 4; or is $C_1$–$C_4$alkyl or $C_1$–$C_4$haloalkyl when n is 1 or 2; or, when n is 1, is nitro, $COR_{11}$, amino, mono-$C_1$–$C_4$alkylamino or di-$C_1$–$C_4$alkylamino;

$R_9$ and $R_{10}$ are each independently of the other hydrogen; or $C_1$–$C_4$alkyl;

$R_9$ and $R_{10}$ together with the linking nitrogen atom are an unsubstituted or a $C_1$–$C_4$alkyl-substituted pyrrolidino or piperidino ring; and $R_{11}$ is $C_1$–$C_4$alkyl; $C_1$–$C_4$haloalkyl; $C_1$–$C_4$alkoxy; phenyl which is substituted by halogen, $C_1$–$C_4$haloalkyl or $C_1$–$C_4$alkoxy; phenyl-$C_1$–$C_2$alkyl or phenyl-$C_1$–$C_2$alkoxy.

10. A fluoran according to claim 8, wherein $R_1$ is hydrogen or methyl;

$R_2$ and $R_3$ are each independently of the other hydrogen; $C_1$–$C_5$alkyl; or $R_2$ and $R_3$ together with the linking nitrogen atom are an unsubstituted pyrrolidino or piperidino ring;

$R_4$ is hydrogen or methyl;

$R_5$ is $COR_{11}$; $CONR_9R_{10}$;

n is 0, 1, 2, 3 or 4;

$R_6$ is halogen when n is 1, 2, 3 or 4; or is nitro or methyl when n is 1 or 2; or, when n is 1, is nitro, amino, mono-$C_1$–$C_4$alkylamino or di-$C_1$–$C_4$alkylamino;

$R_9$ and $R_{10}$ are each independently of the other hydrogen or $C_1$–$C_4$alkyl;

$R_{11}$ is $C_1$–$C_4$alkyl; $C_1$–$C_4$alkoxy; phenyl which is substituted by halogen, $C_1$–$C_4$haloalkyl or $C_1$–$C_4$alkoxy; phenyl-$C_1$–$C_2$alkyl or phenyl-$C_1$–$C_2$alkoxy.

11. A fluoran according to claim 8, wherein $R_5$ is $COR_{11}$.

12. A fluoran according to claim 11, wherein $R_{11}$ is $C_1$–$C_4$alkyl, $C_1$–$C_4$alkoxy or phenyl-$C_1$–$C_2$alkoxy.

13. A fluoran according to claim 11, wherein $R_{11}$ is $C_1$–$C_4$alkoxy or phenyl-$C_1$–$C_2$alkoxy.

14. A fluoran according to claim 8, wherein $R_5$ is $CONR_9R_{10}$.

15. A pressure-sensitive or heat-sensitive recording material comprising a mixture of colour formers with at least one compound of formula I according to claim 1 and a developer.

16. A pressure-sensitive or heat-sensitive recording material comprising a mixture of colour formers with at least one compound of formula I according to claim 8 and a developer.

17. A recording material of claim 1 wherein $R_2$ and $R_3$ are $C_1$–$C_5$alkyl, and $R_5$ is $COR_{11}$ wherein $R_{11}$ is an alkoxy substituent selected from the group consisting of ethoxy, n-propoxy, isoproxy, n-butoxy, sec-butoxy and tert-butoxy.

18. A recording material of claim 17 wherein $R_{11}$ is ethoxy.

19. A recording material of claim 18 wherein $R_2$ and $R_3$ are each ethyl.

20. A recording material of claim 1 wherein $R_1$ and $R_4$ are hydrogen, $R_2$ and $R_3$ are each ethyl, $R_5$ is $COR_{11}$ wherein $R_{11}$ is ethoxy and n is 0.

21. A fluoran of claim 8 wherein $R_2$ and $R_3$ are $C_1$–$C_5$alkyl, and $R_5$ is $COR_{11}$ wherein $R_{11}$ is an alkoxy substituent selected from the group consisting of ethoxy, n-propoxy, isopropoxy, n-butoxy, sec-butoxy and tert-butoxy.

22. A fluoran of claim 21 wherein $R_{11}$ is ethoxy.

23. A fluoran of claim 22 wherein $R_2$ and $R_3$ are each ethyl.

24. A fluoran of claim 23 wherein $R_1$ and $R_4$ are hydrogen.

25. A fluoran of claim 8 wherein $R_1$ and $R_4$ are hydrogen, $R_2$ and $R_3$ are each ethyl, $R_5$ is $COR_{11}$ wherein $R_{11}$ is ethoxy and n is 0.

* * * * *